United States Patent
Nair et al.

(10) Patent No.: US 10,226,050 B2
(45) Date of Patent: Mar. 12, 2019

(54) SYNERGISTIC COMPOSITION OF GERANIUM OIL WITH OTHER ESSENTIAL OILS FOR BEDBUG CONTROL

(71) Applicant: VAMA ECO, INC., San Francisco, CA (US)

(72) Inventors: Krishna Prasad Sudhir Nair, New Delhi (IN); Aharsh Rajeswari Padmananbhan Sasi, New Delhi (IN)

(73) Assignee: VAMA ECO, INC., San Francisco, CA (US)

( * ) Notice: Subject to any disclaimer, the term of this patent is extended or adjusted under 35 U.S.C. 154(b) by 0 days.

(21) Appl. No.: 15/103,811

(22) PCT Filed: Dec. 11, 2014

(86) PCT No.: PCT/US2014/069846
§ 371 (c)(1),
(2) Date: Jun. 10, 2016

(87) PCT Pub. No.: WO2015/089331
PCT Pub. Date: Jun. 18, 2015

(65) Prior Publication Data
US 2016/0309725 A1    Oct. 27, 2016

Related U.S. Application Data

(60) Provisional application No. 61/914,696, filed on Dec. 11, 2013.

(51) Int. Cl.

| | | |
|---|---|---|
| *A61K 36/00* | (2006.01) | |
| *A01N 65/08* | (2009.01) | |
| *A01N 65/22* | (2009.01) | |
| *A01N 65/00* | (2009.01) | |
| *A01N 65/26* | (2009.01) | |
| *A01N 65/28* | (2009.01) | |
| *A01N 25/08* | (2006.01) | |
| *A01N 25/30* | (2006.01) | |
| *A01N 65/24* | (2009.01) | |
| *A01N 65/36* | (2009.01) | |
| *A01N 65/44* | (2009.01) | |
| *A47C 31/00* | (2006.01) | |
| *A47C 31/10* | (2006.01) | |
| *A47G 9/00* | (2006.01) | |
| *A47G 9/02* | (2006.01) | |
| *A47G 9/10* | (2006.01) | |
| *A47G 27/02* | (2006.01) | |
| *A47K 10/02* | (2006.01) | |
| *B65D 83/14* | (2006.01) | |

(52) U.S. Cl.
CPC ............. *A01N 65/08* (2013.01); *A01N 25/08* (2013.01); *A01N 25/30* (2013.01); *A01N 65/00* (2013.01); *A01N 65/22* (2013.01); *A01N 65/24* (2013.01); *A01N 65/26* (2013.01); *A01N 65/28* (2013.01); *A01N 65/36* (2013.01); *A01N 65/44* (2013.01); *A47C 31/007* (2013.01); *A47C 31/105* (2013.01); *A47G 9/007* (2013.01); *A47G 9/0223* (2013.01); *A47G 9/0238* (2013.01); *A47G 9/0253* (2013.01); *A47G 9/10* (2013.01); *A47G 27/02* (2013.01); *A47K 10/02* (2013.01); *B65D 83/752* (2013.01); *A47G 2009/001* (2013.01)

(58) Field of Classification Search
CPC ...................................................... A61K 36/00
See application file for complete search history.

(56) References Cited

U.S. PATENT DOCUMENTS

| | | | | |
|---|---|---|---|---|
| 2007/0065053 | A1* | 3/2007 | Feinberg | B65F 1/0006 383/105 |
| 2009/0313883 | A1* | 12/2009 | Olson | A01M 1/023 43/131 |
| 2013/0034619 | A1 | 2/2013 | Breyner | |
| 2013/0122120 | A1 | 5/2013 | Angjeli | |
| 2013/0295153 | A1 | 11/2013 | Miresmailli et al. | |

FOREIGN PATENT DOCUMENTS

WO    2013050967 A1    4/2013

OTHER PUBLICATIONS

International Searching Authority, United States; PCT International Search Report & Written Opinion of PCT Application No. PCT/US14/69846; Nov. 3, 2015; 14 pages; United States.

* cited by examiner

*Primary Examiner* — Qiuwen Mi
(74) *Attorney, Agent, or Firm* — Foley & Lardner LLP

(57) ABSTRACT

Methods and compositions for controlling bedbugs are provided.

19 Claims, 17 Drawing Sheets

| DOSE | Cumulative % mortality of First Instar Cimex lectularius exposed to various doses of Formula A | | | | | | | |
|---|---|---|---|---|---|---|---|---|
| | Day1 | Day2 | Day3 | Day4 | Day5 | Day6 | Day7 | Day8 |
| 0 g/sq.m | 0 | 1 | 2.5 | 5 | 5 | 7 | 10 | 10 |
| 1 g/sq.m | 12 | 47 | 88 | 97.6 | 98.3 | 99.1 | 99.8 | 100 |
| 3 g/sq.m | 75.3 | 89 | 95.6 | 98 | 98.9 | 99.5 | 99.8 | 100 |
| 5 g/sq.m | 89 | 95 | 98.8 | 99.4 | 99.7 | 100 | 100 | 100 |
| 8 g/sq.m | 95 | 99.1 | 100 | 100 | 100 | 100 | 100 | 100 |

FIGURE 1C

| | Cumulative % mortality of Adult Cimex lectularius exposed to various doses of Formula A | | | | | | | | | | | |
|---|---|---|---|---|---|---|---|---|---|---|---|---|
| DOSE | Day1 | Day2 | Day3 | Day4 | Day5 | Day6 | Day7 | Day8 | Day9 | Day10 | Day11 | Day12 |
| 0 g/sq.m | 0 | 2.2 | 2.2 | 5.1 | 7.5 | 7.5 | 12.5 | 15 | 15.9 | 17 | 17.5 | 22.5 |
| 1 g/sq.m | 27.5 | 39 | 66.2 | 75 | 75.6 | 81.5 | 90.4 | 96 | 96 | 99 | 99.8 | 100 |
| 3 g/sq.m | 45.5 | 56 | 70 | 76.9 | 80 | 85.3 | 90.8 | 95.6 | 98.2 | 99.1 | 99.6 | 100 |
| 5 g/sq.m | 87 | 88.5 | 93.1 | 95 | 95.6 | 98.8 | 99 | 99.4 | 100 | 100 | 100 | 100 |
| 8 g/sq.m | 92.2 | 95.6 | 96 | 98.4 | 99 | 100 | 100 | 100 | 100 | 100 | 100 | 100 |

| | Cumulative % mortality of First Instar Cimex lectularius exposed to various doses of Formula B | | | | | | | |
|---|---|---|---|---|---|---|---|---|
| DOSE | Day1 | Day2 | Day3 | Day4 | Day5 | Day6 | Day7 | Day8 |
| 0 g/sq.m | 0 | 2 | 2 | 5 | 7 | 7 | 10 | 11 |
| 1 g/sq.m | 10 | 51 | 85 | 98 | 99.1 | 99.6 | 100 | 100 |
| 3 g/sq.m | 79.2 | 87.5 | 96.7 | 97.6 | 98 | 99.4 | 99.8 | 100 |
| 5 g/sq.m | 90 | 92.4 | 98 | 98.5 | 99.8 | 100 | 100 | 100 |
| 8 g/sq.m | 96.2 | 99.8 | 100 | 100 | 100 | 100 | 100 | 100 |

FIGURE 2C

| | Cumulative % mortality of Adult Cimex lectularius exposed to various doses of Formula B | | | | | | | | | | | |
|---|---|---|---|---|---|---|---|---|---|---|---|---|
| DOSE | Day1 | Day2 | Day3 | Day4 | Day5 | Day6 | Day7 | Day8 | Day9 | Day10 | Day11 | Day12 |
| 0 g/sq.m | 0 | 2 | 2.5 | 4 | 6.7 | 7.5 | 12 | 15 | 15 | 17.5 | 17.5 | 20 |
| 1 g/sq.m | 30.2 | 46.1 | 69 | 77.3 | 79.8 | 83.1 | 91 | 95.5 | 98 | 98.5 | 99.1 | 100 |
| 3 g/sq.m | 44 | 57.2 | 71 | 76.5 | 83 | 89 | 92.4 | 96.5 | 98 | 99.5 | 100 | 100 |
| 5 g/sq.m | 90 | 90 | 95.5 | 95.5 | 98 | 98.5 | 99 | 99.5 | 100 | 100 | 100 | 100 |
| 8 g/sq.m | 93.5 | 96 | 96.5 | 99 | 99.5 | 100 | 100 | 100 | 100 | 100 | 100 | 100 |

| DOSE | Cumulative % mortality of First Instar Cimex lectularius exposed to various doses of Formula C | | | | | | | |
|---|---|---|---|---|---|---|---|---|
| | Day1 | Day2 | Day3 | Day4 | Day5 | Day6 | Day7 | Day8 |
| 0 g/sq.m | 0 | 1.7 | 1.7 | 4.5 | 8 | 8 | 12 | 12 |
| 1 g/sq.m | 13 | 47.5 | 83.2 | 97 | 99 | 99.5 | 99.5 | 100 |
| 3 g/sq.m | 77.8 | 85 | 94.5 | 97 | 97.5 | 99 | 99.5 | 100 |
| 5 g/sq.m | 88.7 | 91.6 | 96 | 99 | 99.4 | 100 | 100 | 100 |
| 8 g/sq.m | 96.6 | 99.4 | 100 | 100 | 100 | 100 | 100 | 100 |

| DOSE | Cumulative % mortality of Adult Cimex lectularius exposed to various doses of Formula C | | | | | | | | | | | |
|---|---|---|---|---|---|---|---|---|---|---|---|---|
| | Day1 | Day2 | Day3 | Day4 | Day5 | Day6 | Day7 | Day8 | Day9 | Day10 | Day11 | Day12 |
| 0 g/sq.m | 1 | 1 | 2.2 | 3 | 6 | 6 | 8 | 12.5 | 16.2 | 18 | 18 | 22 |
| 1 g/sq.m | 31.6 | 48.2 | 68.4 | 80 | 80 | 85.5 | 93.5 | 97 | 99 | 99 | 99.5 | 100 |
| 3 g/sq.m | 50.4 | 65.6 | 75 | 77 | 85.6 | 91.8 | 95 | 99 | 99.5 | 100 | 100 | 100 |
| 5 g/sq.m | 92 | 94.5 | 97 | 97 | 98.6 | 99 | 99.6 | 100 | 100 | 100 | 100 | 100 |
| 8 g/sq.m | 95.2 | 96 | 96.5 | 98.5 | 99.7 | 100 | 100 | 100 | 100 | 100 | 100 | 100 |

| DOSE | Cumulative % mortality of First Instar Cimex lectularius exposed to various doses of Formula D | | | | | | | |
|---|---|---|---|---|---|---|---|---|
| | Day1 | Day2 | Day3 | Day4 | Day5 | Day6 | Day7 | Day8 |
| 0 g/sq.m | 0 | 2 | 2.5 | 4 | 5 | 8 | 10 | 12 |
| 1 g/sq.m | 11.8 | 45.5 | 80.7 | 94.6 | 97 | 98.2 | 99.5 | 100 |
| 3 g/sq.m | 77.3 | 88.5 | 96 | 97.5 | 98 | 99 | 99.5 | 100 |
| 5 g/sq.m | 87 | 92 | 98.5 | 99 | 99.5 | 100 | 100 | 100 |
| 8 g/sq.m | 93.6 | 99.1 | 99.8 | 100 | 100 | 100 | 100 | 100 |

FIGURE 4C

| | Cumulative % mortality of Adult Cimex lectularius exposed to various doses of Formula D | | | | | | | | | | | |
|---|---|---|---|---|---|---|---|---|---|---|---|---|
| DOSE | Day1 | Day2 | Day3 | Day4 | Day5 | Day6 | Day7 | Day8 | Day9 | Day10 | Day11 | Day12 |
| 0 g/sq.m | 0 | 2 | 4 | 4 | 6 | 7.5 | 13 | 15 | 15 | 17 | 17.5 | 21 |
| 1 g/sq.m | 25.5 | 37.9 | 67.8 | 73.2 | 75 | 80.5 | 87.9 | 95 | 97.5 | 98.7 | 99.5 | 100 |
| 3 g/sq.m | 49 | 57.7 | 68.5 | 74.4 | 79.7 | 86 | 91.2 | 94 | 97.5 | 98.7 | 99.8 | 100 |
| 5 g/sq.m | 89.3 | 91 | 94.5 | 96 | 97.5 | 99 | 99.2 | 99.7 | 100 | 100 | 100 | 100 |
| 8 g/sq.m | 95 | 96.5 | 97.3 | 99 | 99.5 | 100 | 100 | 100 | 100 | 100 | 100 | 100 |

|  | Cumulative % mortality of First Instar Cimex lectularius exposed to various doses of Formula E | | | | | | | |
|---|---|---|---|---|---|---|---|---|
| DOSE | Day1 | Day2 | Day3 | Day4 | Day5 | Day6 | Day7 | Day8 |
| 0 g/sq.m | 0 | 2 | 2.5 | 5 | 5 | 7.5 | 10 | 12 |
| 1 g/sq.m | 20 | 52.3 | 79.2 | 95 | 97.5 | 99 | 99.5 | 100 |
| 3 g/sq.m | 78 | 82 | 91.3 | 94 | 96.7 | 98.8 | 99.3 | 100 |
| 5 g/sq.m | 85.9 | 90.5 | 95.6 | 97.5 | 99.5 | 100 | 100 | 100 |
| 8 g/sq.m | 94.9 | 98.5 | 100 | 100 | 100 | 100 | 100 | 100 |

FIGURE 5C

| | Cumulative % mortality of Adult Cimex lectularius exposed to various doses of Formula E | | | | | | | | | | | |
|---|---|---|---|---|---|---|---|---|---|---|---|---|
| DOSE | Day1 | Day2 | Day3 | Day4 | Day5 | Day6 | Day7 | Day8 | Day9 | Day10 | Day11 | Day12 |
| 0 g/sq.m | 0 | 2 | 2 | 4 | 5 | 7.5 | 7.5 | 12.5 | 15 | 17.5 | 20 | 22 |
| 1 g/sq.m | 35 | 51.5 | 69 | 79.5 | 82.6 | 89 | 95 | 98 | 98 | 99.5 | 99.5 | 100 |
| 3 g/sq.m | 49.2 | 63.2 | 76.5 | 79 | 86 | 93 | 96.5 | 98.2 | 99.2 | 100 | 100 | 100 |
| 5 g/sq.m | 91 | 95 | 96.5 | 98 | 99 | 99.5 | 99.6 | 100 | 100 | 100 | 100 | 100 |
| 8 g/sq.m | 96.1 | 97.5 | 98 | 99 | 99.8 | 100 | 100 | 100 | 100 | 100 | 100 | 100 |

| DOSE | Cumulative % mortality of First Instar Cimex lectularius exposed to various doses of Formula F | | | | | | | |
|---|---|---|---|---|---|---|---|---|
| | Day1 | Day2 | Day3 | Day4 | Day5 | Day6 | Day7 | Day8 |
| 0 g/sq.m | 0 | 2 | 2.5 | 4 | 5 | 7 | 12 | 12 |
| 1 g/sq.m | 15 | 48 | 85.6 | 96.7 | 98 | 99 | 99.7 | 100 |
| 3 g/sq.m | 75 | 87.5 | 94.3 | 97.5 | 98.5 | 99 | 99.7 | 100 |
| 5 g/sq.m | 89.3 | 95 | 98.6 | 99.3 | 99.8 | 100 | 100 | 100 |
| 8 g/sq.m | 96.2 | 98.9 | 100 | 100 | 100 | 100 | 100 | 100 |

FIGURE 6C

| | \multicolumn{12}{c|}{Cumulative % mortality of Adult Cimex lectularius exposed to various doses of Formula F} |
|---|---|---|---|---|---|---|---|---|---|---|---|---|
| DOSE | Day1 | Day2 | Day3 | Day4 | Day5 | Day6 | Day7 | Day8 | Day9 | Day10 | Day11 | Day12 |
| 0 g/sq.m | 0 | 2 | 3 | 3 | 6 | 7.5 | 12.5 | 12.5 | 15 | 17.5 | 20 | 22 |
| 1 g/sq.m | 26.7 | 36 | 60 | 74 | 76.4 | 80.9 | 93 | 95 | 98.5 | 99 | 99.8 | 100 |
| 3 g/sq.m | 44.5 | 60 | 69.6 | 78.4 | 83 | 89.2 | 93 | 96.5 | 98.5 | 99 | 99.5 | 100 |
| 5 g/sq.m | 87.2 | 90 | 93 | 94 | 97.2 | 98 | 99.5 | 99.8 | 100 | 100 | 100 | 100 |
| 8 g/sq.m | 94 | 97.7 | 98.5 | 99 | 99.8 | 100 | 100 | 100 | 100 | 100 | 100 | 100 |

SYNERGISTIC COMPOSITION OF GERANIUM OIL WITH OTHER ESSENTIAL OILS FOR BEDBUG CONTROL

CROSS REFERENCE TO RELATED APPLICATIONS

This application is a U.S. National Phase Application under 37 CFR § 371 of International Application Serial No. PCT/US2014/069846, filed Dec. 11, 2014, which claims priority to U.S. Provisional Application Ser. No. 61/914,696, filed Dec. 11, 2013, each of which is incorporated herein by reference in its entirety.

FIELD

The present invention relates to an aqueous formulation for control of bedbugs. More particularly, the invention relates to a formulation comprising of geranium oil and two or more essential oils and/or plant extracts with natural surfactants in water for the treatment and control of bedbugs.

BACKGROUND

Heretofore, a number of insecticides have been proposed for killing/repelling bedbugs. Even though many such insecticides are effective in killing/repelling bedbugs, their toxicity towards non-targeted living organisms has been a major concern. Potent insecticides such as DDT (dichlorodiphenyltrichloroethane) to weaker insecticides such as pyrethroids have been used to control the bedbug nuisance. Drawbacks of these synthetic insecticides include development of resistance leading to reduced efficacy over time, carcinogenicity to humans and domestic animals, and other detrimental side effects.

Bedbugs are members of the genus *Cimex*, of which *Cimex lectularius* (the common bed bug) is the best known, as it prefers to feed on human blood. Other *Cimex* species are specialized to other animals, e.g., bat bugs, *Cimex pipistrelli* (Europe), *Cimex pilosellus* (western US), and *Cimex adjunctus* (entire eastern US). The name of the "bed bug" is derived from the preferred habitat of *Cimex lectularius*: warm houses, especially near or inside of beds, bedding, or other sleep areas.

Various formulation disclosed in the prior art make use of compositions of essential oils as insect repellents. Such formulation comprise of different individual oils or blend of essential oils such as thyme oil, lilac oil, basil oil, neem oil, citronella oil, catnip oil, celery seed oil, lavender oil, lime oil, pennyroyal, lemon grass oil, fennal oil, cedar oil, clove oil, sandalwood, or peppermint oil. Oils in combination with one another may repel some insects, and some are effective at killing insects due to chemo-receptor binding properties. However, these oils lack efficacy in the control of insects at lower oil concentrations.

There is, therefore, a need for a safe and effective insecticide based on naturally occurring substances to control bed bugs.

SUMMARY OF THE INVENTION

The present invention according to some embodiments provides a synergistic composition comprising geranium oil in combination with other essential oils that control bed bugs. Such compositions are eco-friendly, entirely biodegradable, safe and non-toxic to humans and other non-target organisms. In one embodiment, the composition further comprises a surface active agent. In one embodiment, the composition is an oil-in-water emulsion. In one embodiment, the composition is an aqueous formulation. In one embodiment, the composition is in a concentrated formulation. In one embodiment, the composition is in a ready-to-use formulation.

The present invention further provides methods of controlling a bed bug infestation using a composition comprising geranium oil and other essential oils such that the need for repeated application of the composition is minimized by maintaining the effectiveness of the composition over a period of time after the initial application. In one embodiment, application of the composition kills bed bugs. In one embodiment, application of the composition controls bed bugs (i.e., controls an infestation of bed bugs).

The present invention according to some embodiments provides synergistic compositions of geranium oil with other essential oils to control bed bugs, wherein the active synergistic composition can be employed in a reduced amount and still achieve the desired control over the target organisms.

This invention is based, in part, on the surprising discovery that geranium oil, in combination with one or more essential oils, is effective at killing bed bugs. In accordance with this discovery, it is an object of the invention to provide essential oil compositions that are effective against *Cimex lectularius*.

Without being bound by theory, it is believed that the insecticidal action of essential oils is mainly due to the binding of its constituents at various receptor sites, thereby inhibiting or activating neuron transmission. They are effective for the disruption of receptors, including but not limited to, one or more of cyclic adenosine monophosphate (cAMP)/cAMP-dependent protein kinase, tyrosine kinase, MEK 1 or MEK 2, calcium phospholipid-dependent protein kinase (PKC), mitogen activated protein kinase family members, calcium-calmodulin-dependent protein kinase, growth factor receptor, and octopamine receptor. This neuron toxicity is enhanced when the geranium oil is combined with a specific blend of essential oils and/or plant extracts. Without being bound by theory, it is believed that essential oils antagonize the target organism's nerve receptors, disrupt cellular calcium levels within the target organism, or bind the olfactory receptors of the target organism. In any event, the net effect of the increased toxicity and synergized action of the inventive synergistic composition disclosed herein is heretofore unknown and unexpected.

In accordance with this discovery, it is another object of the invention to provide a method for treating areas and mammals affected by bed bugs.

Other objects and advantages of this invention will become readily apparent from the ensuing description.

BRIEF DESCRIPTION OF THE DRAWINGS

FIGS. 1A, 1B, 1C and 1D: FIGS. 1A and 1B show results of experiments designed to establish optimal dose rates of Formulation A as determined by percent mortality of first instar and adult bedbugs. FIG. 1A shows the cumulative % mortality of first instar *Cimex lectularius* exposed to the indicated doses of Formulation A; FIG. 1B is a graphical representation of data from FIG. 1A; FIG. 1C shows the cumulative % mortality of adult *Cimex lectularius* exposed to the indicated doses of Formulation A; FIG. 1D is a graphical representation of data from FIG. 1C.

FIGS. 2A, 2B, 2C and 2D: FIGS. 2A and 2B show results of experiments designed to establish optimal dose rates of Formulation B as determined by percent mortality of first instar and adult bedbugs. FIG. 2A shows the cumulative % mortality of first instar *Cimex lectularius* exposed to various doses of Formulation B; FIG. 2B is a graphical representation of data from FIG. 2A; FIG. 2C shows the cumulative % mortality of adult *Cimex lectularius* exposed to various doses of Formulation B; FIG. 2D is a graphical representation of data from FIG. 2C.

FIGS. 3A and 3B show results of experiments designed to establish optimal dose rates of Formulation C as determined by percent mortality of first instar and adult bedbugs. FIG. 3A shows the cumulative % mortality of first instar *Cimex lectularius* exposed to the indicated doses of Formulation C; FIG. 3B is a graphical representation of data from FIG. 3A; FIG. 3C shows the cumulative % mortality of adult *Cimex lectularius* exposed to the indicated doses of Formulation C; FIG. 3D is a graphical representation of data from FIG. 3C.

FIGS. 4A, 4B, 4C and 4D: FIGS. 4A and 4B show results of experiments designed to establish optimal dose rates of Formulation D as determined by percent mortality of first instar and adult bedbugs. FIG. 4A shows the cumulative % mortality of first instar *Cimex lectularius* exposed to the indicated doses of Formulation D. FIG. 4B is a graphical representation of data from FIG. 4A; FIG. 4C shows the cumulative % mortality of adult *Cimex lectularius* exposed to the indicated doses of Formulation D; FIG. 4D is a graphical representation of data from FIG. 4C.

FIGS. 5A, 5B, 5C and 5D: FIGS. 5A and 5B show results of experiments designed to establish optimal dose rates of Formulation E as determined by percent mortality of first instar and adult bedbugs. FIG. 5A shows the cumulative % mortality of first instar *Cimex lectularius* exposed to the indicated doses of Formula E; FIG. 5B is a graphical representation of data from FIG. 5A; FIG. 5C shows the cumulative % mortality of adult *Cimex lectularius* exposed to the indicated doses of Formula E; FIG. 5D is a graphical representation of data from FIG. 5C.

FIGS. 6A, 6B, 6C and 6D: FIGS. 6A and 6B shows results of experiments designed to establish optimal dose rates of Formulation F as determined by percent mortality of first instar and adult bedbugs. FIG. 6A shows the cumulative % mortality of first instar *Cimex lectularius* exposed to the indicated doses of Formulation F; FIG. 6B is a graphical representation of data from FIG. 6A; FIG. 6C shows the cumulative % mortality of adult *Cimex lectularius* exposed to the indicated doses of Formulation F; FIG. 6D is a graphical representation of data from FIG. 6C.

DETAILED DESCRIPTION OF THE INVENTION

Figures 1A, 1B:
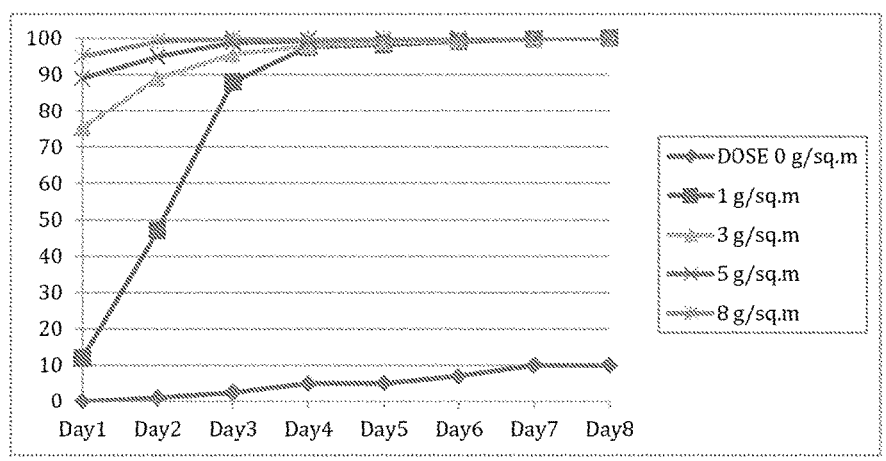

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

The detailed description of the invention is divided into various sections only for the reader's convenience and disclosure found in any section may be combined with that in another section. Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "an essential oil" includes a plurality of essential oils.

Definitions As used herein, the term "essential oil" refers to a concentrated hydrophobic liquid containing volatile aroma compounds from plants. Essential oils are also known as volatile oils, ethereal oils, or aetherolea, or simply as the "oil of" the plant from which they were extracted, such as oil of clove. An oil is "essential" in the sense that it carries a distinctive scent, or essence, of the plant.

Percentages recited herein indicate percentage by volume (v/v), unless otherwise noted. Percentages recited herein indicate the final concentration of the component in the ready-to-use composition. That is, a concentrated formulation of the composition will comprise a higher concentration of each ingredient (e.g., essential oil and/or surfactant) such that it is diluted (e.g., with water) to the final concentration prior to use.

Compositions

The present invention according to some embodiments relates to novel synergistic compositions of geranium oil with other essential oils for insect control. In one aspect, the composition as described herein is used to control bed bugs. In a preferred embodiment, the formulation is effective against *Cimex lectularius* bed bugs.

In one aspect, the invention relates to a composition for controlling a target insect (e.g., bed bugs), the composition comprising essential oils wherein at least one essential oil is geranium oil.

Geranium essential oil is extracted from the plant *Pelargonium odorantissimum*, of the Geraniaceae family, and is composed of various chemical constituents. Geranium essential oil comprises, without limitation, one or more of a-pinene, myrcene, limonene, menthone, linalool, geranyl acetate, citronellol, geraniol, and geranyl butyrate.

The other essential oils used to synergize the activity of geranium oil generally contain, as a major constituent, an acyclic monoterpene alcohol or aldehyde, a benzenoid aromatic compound containing at least one oxygenated substituent or side chain, or a monocarbocyclic terpene generally having a six membered ring bearing one or more oxygenated substituents.

Apart from these major constituents, there are a number of other components also available in each essential oil. Some examples of the major constituents of plant extracts which are used in this invention are as follows:

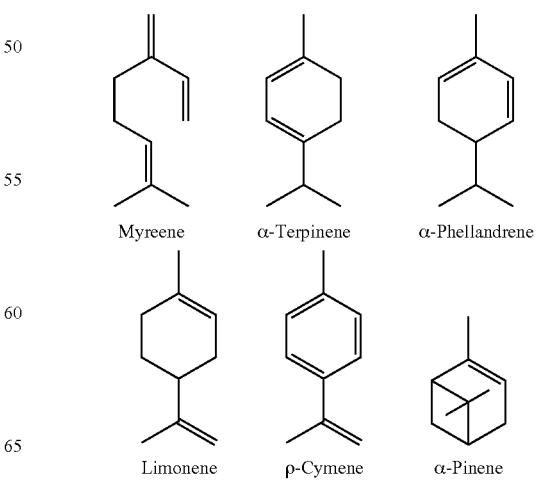

-continued

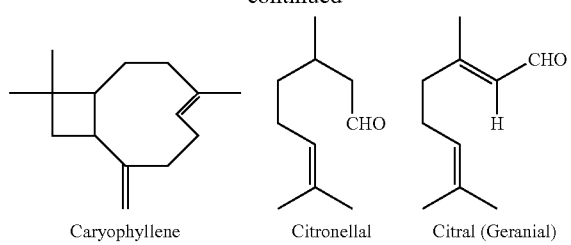
Caryophyllene   Citronellal   Citral (Geranial)

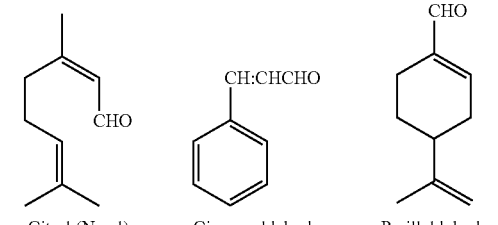
Citral (Neral)   Cinnamaldehyde   Perillaldehyde

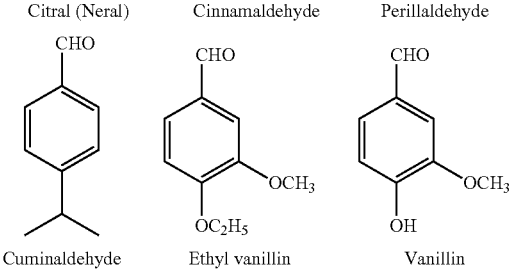
Cuminaldehyde   Ethyl vanillin   Vanillin

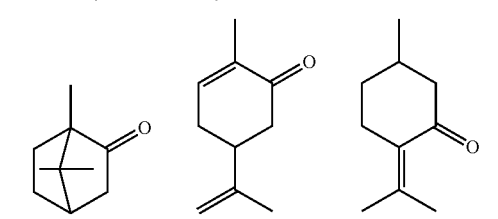
Camphor   Carvone   Pulegone

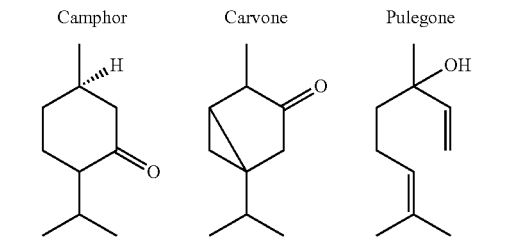
Menthone   Thujone   Linalool

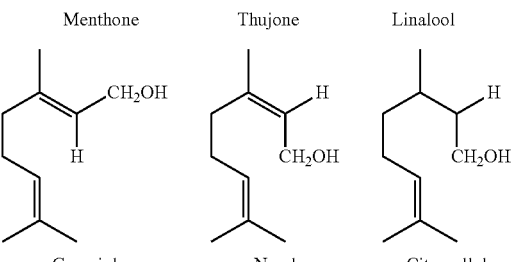
Geraniol   Nerol   Citronellol

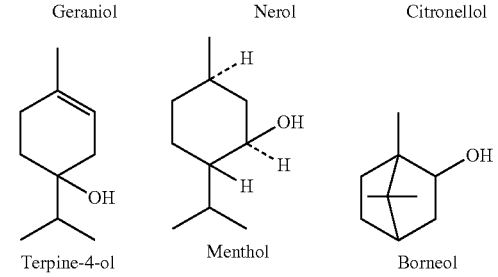
Terpine-4-ol   Menthol   Borneol

-continued

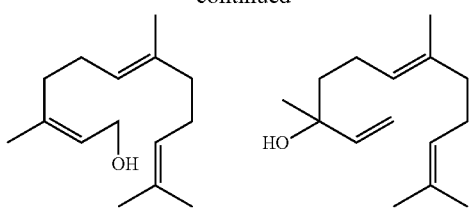
Farnesol   Nerolidol

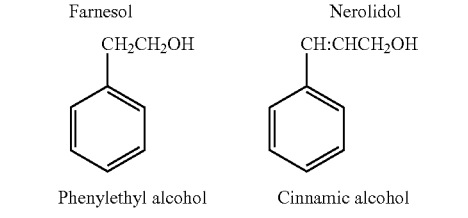
Phenylethyl alcohol   Cinnamic alcohol

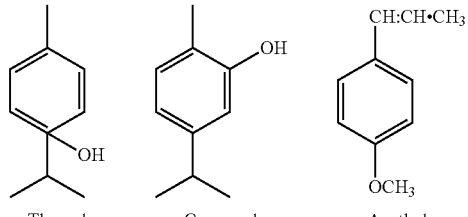
Thymol   Carvacrol   Anethole

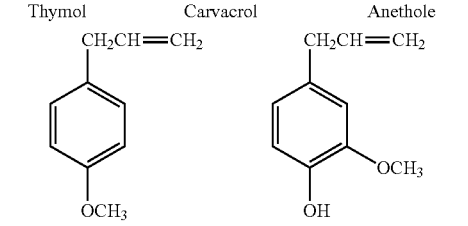
Estragol   Eugenol

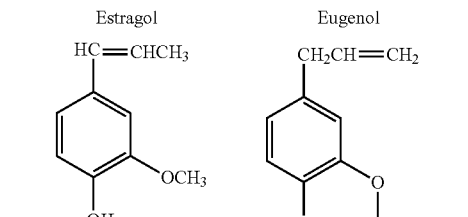
Isoeugenol   Safrol

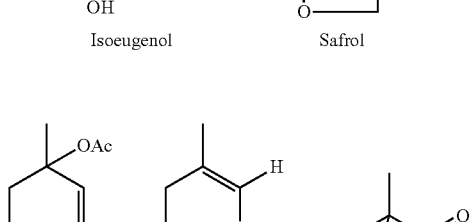
Linalyl acetate   Neryl acetate   Fenehone

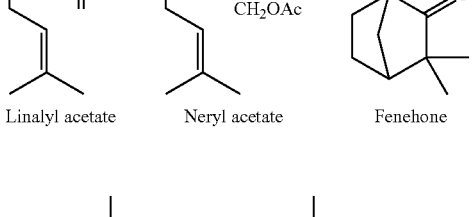
Citronellyl acetate   1,8 Cineole

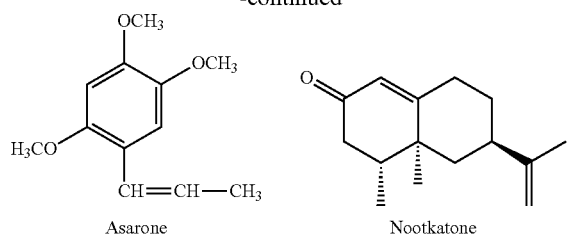
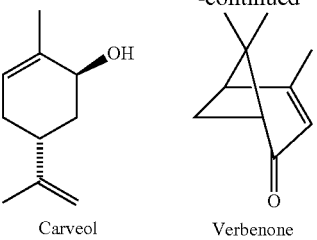
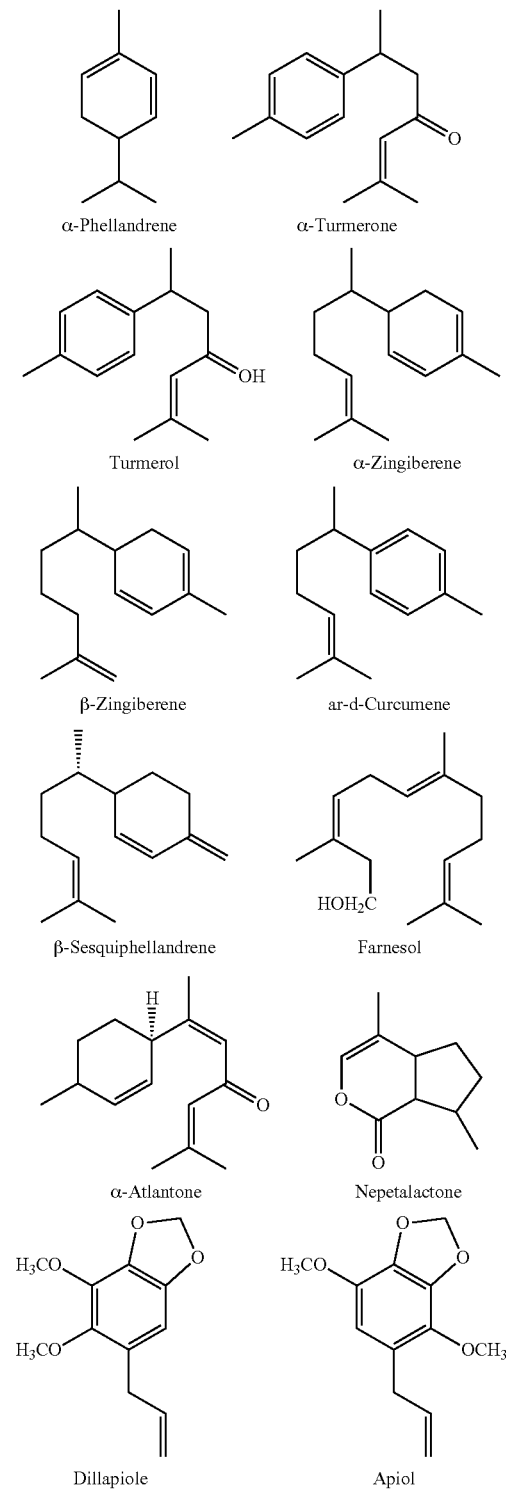

It should be understood that in some embodiments, one or more of the above mentioned constituents can be specifically excluded from the compositions and methods.

In one aspect, the composition of the present invention is a synergistic composition comprising geranium oil and at least one plant extract, plant derived fragrance, flavor, or color. In one embodiment, the final concentration of geranium oil is between about 0.1% and about 10% (v/v), or any sub value or sub range there between. In one embodiment, the final concentration of geranium oil is between about 0.5% and about 8% (v/v). In one embodiment, the final concentration of geranium oil is between about 1% and about 5%. In a preferred embodiment, the formulation comprises geranium oil at a final concentration of about 0.5% to about 4.9% by volume.

In one aspect of the invention, the composition further comprises additional plant essential oils selected from one or more of clove oil, orange oil, eucalyptus oil, peppermint oil, cedar wood oil, neem oil, cinnamon bark oil, lemon grass oil, tea tree oil, and lavender oil. In some embodiments, one or more of the essential oils mentioned herein can be specifically excluded from the compositions and methods. In one embodiment, the composition comprises geranium oil and one or more additional essential oils. In a preferred embodiment, the composition comprises geranium oil and two or more additional essential oils. In one embodiment, the final concentration of the additional essential oil(s) is between about 0.1% and about 10% (v/v) or any sub value or sub range there between. In one embodiment, the final concentration of the additional essential oil(s) is between about 0.5% and about 8% (v/v). In one embodiment, the final concentration of the additional essential oil(s) is between about 1% and about 5% (v/v).

In a preferred embodiment, the final concentration of all essential oil(s) in the composition is between about 0.5% and about 4.9% by volume, including geranium oil and excluding surfactants, or any sub value or sub range there between. In one embodiment, the formulation contains peppermint oil at a final concentration of about 0.7% to about 2.9%. In one embodiment, the formulation contains eucalyptus oil at a final concentration of about 0.4% to about 1.2%. In one embodiment, the formulation contains clove oil at a final concentration of about 0.8% to about 0.9%. In one embodiment, the formulation contains cinnamon oil at a final concentration of about 0.7% to about 0.9%. In one embodiment, the formulation contains lavender oil at a final concentration of about 0.6% to about 1.4%. In one embodiment, the formulation contains neem oil at a final concentration of about 0.5% to about 1%. In one embodiment, the formulation contains orange oil at a final concentration of about 0.7%. In one embodiment, the formulation contains cedar wood oil at a final concentration of about 0.4% to about 0.5%. In one embodiment, the formulation contains lemon grass oil at a final concentration of about 0.4% to about 0.5%.

In an especially preferred embodiment, the composition further comprises a surface active agent (surfactant). In one embodiment, the natural surfactant is present at a final concentration of about 0.5% to about 4.5% by volume or any sub value or sub range there between. In one embodiment, the surfactant is present at a final concentration of about 1% to about 4% by volume.

Herein the term "surfactant" refers to a compound that lowers the surface tension between two liquids or between a liquid and a solid. Surfactants may act as detergents, wetting agents, emulsifiers, foaming agents, and/or dispersants. Herein, the surfactant allows the oils to disperse in water. The natural surface acting agent/surfactants, within which the plant extracts can be solubilized, at least serves as an adjuvant and in some instances acts as a co-active ingredient.

In a preferred embodiment, the surfactant is a non-toxic surfactant. Non-limiting examples of non-toxic surfactants include ceteareth-25, cocamide MEA, cocamidopropyl betaine, coceth-4, coceth-7, coconut alcohol ethoxylate, hydroxyethelcellulose, lauryl polyglucose, pareth-7, polyglucose, polyglucoside, PPG-10-Laureth-7, PPG-4-Laureth-8, PPG-6 C12-15-Pareth-12, sodium lauraminopropionate, sodium laureth sulphate, sodium lauryl sulphate, and castor oil.

In a preferred embodiment, the surface active agent is a natural surfactant. The natural surfactant may also possess a synergistic effect with the essential oil(s) and contribute to stability of this formulation. In one embodiment, the natural surfactant is activated castor oil or sodium lauryl sulfate (SLS).

In a preferred embodiment, said surface active agent is castor oil. Castor oil is a vegetable oil obtained by pressing the seeds of the Castor plant (*Ricinus communis*).

In still another embodiment, the castor oil is activated. In a preferred embodiment, the castor oil is ethoxylated (i.e., subjected to an ethoxylation process using castor oil and ethylene oxide). Activated castor oil is also referred to as ethoxylated castor oil. Castor oil is a non-ionic surfactant that is widely used in oral, topical, and prescription formulations. In one embodiment, activated castor oil is employed as an emulsifying or solubilising agent.

In still another preferred embodiment, the surface active agent is SLS. SLS is an organic compound with the formula $CH_3(CH_2)_{11}OSO_3Na$. It is an anionic surfactant used in many cleaning and hygiene products. The salt is of an organosulfate consisting of a 12-carbon tail attached to a sulfate group, giving the material the amphiphilic properties required of a detergent. Being derived from inexpensive coconut and palm oils, it is a common component of many domestic cleaning products.

The compositions of the present invention may be prepared in a variety of forms, including but not limited to oil-in-water emulsion, aqueous formulation, or aerosol formulation. In one embodiment, the composition is a concentrated formulation. In one embodiment, the concentrated formulation is diluted (e.g., with water) to the final concentration prior to use. In one embodiment, the composition is a diluted (i.e., ready-to-use) formulation.

In one embodiment the composition is in the form of an oil-in-water emulsion. In one embodiment, water is present in the oil-in-water emulsion at a final concentration of about 90% to about 99.5% by volume or any sub value or sub range there between.

In a specific embodiment of the invention, the composition is provided in a concentrated formulation, comprising (1) about 20% to about 30% percent (v/v) of one or more essential oils; (2) about 20% to about 30% (v/v) of a geranium oil; and (3) about 40% to about 60% (v/v) of a natural surface acting agent (surfactant). In a preferred embodiment, the concentrate is diluted with water at a ratio of about 1:50 to about 1:500, and preferably from about 1:10 to about 1:50, to yield a ready-to-use formulation. For any of the ranges or concentrations provided, also contemplated is any sub value or sub range there between.

The compositions of the present invention can be applied to a target area in a number of ways, including but not limited to spraying, misting, and dropping.

In one embodiment, this invention further encompasses an application device comprising the composition as described herein. The application device may be any suitable device for applying liquid insecticide. In one embodiment, the application device is selected from the group consisting of a spray bottle, an aerosolized spray can, a foam applicator, a fogger, and a compression sprayer.

The present invention provides an effective formulation that includes essential oils and/or plant extracts. In one embodiment, the composition provides complete control over bed bugs and provides a healthy living condition for humans. The ability to effectively control the target insect (e.g., bed bugs) using a very dilute preparation results in significant cost saving over current insect control solutions.

The insecticidal composition of the invention can be prepared in various forms, including sprayable liquids and aerosols. A sprayable liquid form is preferred. Liquid compositions may be prepared in a concentrated form or in a ready-to-use form. A concentrated formulation is primarily a emulsifiable composition in which the castor oil is believed to contribute some level of activity, and is also a solvent and a carrier for the geranium oil and additional essential oil(s). This composition can be diluted with water before application. Ready-to-use formulations are stable aqueous emulsions in which water is the primary ingredient, yet the geranium oil and other essential oil(s) are present at sufficient concentrations to provide bed bug control.

Exemplary (but non-limiting) formulations are given below. Concentrations are provided as the final concentration (i.e., concentration at which the formulation is applied to a target area).

Formulation (A)

| Components | Percentage (%) |
| --- | --- |
| Geranium Oil | 3 |
| Peppermint Oil | 0.8 |
| Eucalyptus Oil | 0.4 |
| Clove Oil | 0.9 |
| Cinnamon bark Oil | 0.8 |
| Surfactant | 2 |
| Water | Rest |

Formulation (B)

| Components | Percentage (%) |
| --- | --- |
| Geranium Oil | 2.9 |
| Neem Oil | 1 |
| Orange Oil | 0.7 |
| Eucalyptus Oil | 0.4 |
| Clove Oil | 0.8 |
| Surfactant | 4 |
| Water | Rest |

Formulation (C)

| Components | Percentage (%) |
| --- | --- |
| Geranium Oil | 4 |
| Neem Oil | 0.5 |
| Peppermint Oil | 1.1 |
| Eucalyptus Oil | 0.9 |
| Lavender Oil | 0.6 |
| Cedarwood Oil | 0.4 |
| Surfactant | 1.5 |
| Water | Rest |

Formulation (D)

| Components | Percentage (%) |
| --- | --- |
| Geranium Oil | 2 |
| Lavender Oil | 1.2 |
| Eucalyptus Oil | 1.2 |
| Peppermint Oil | 0.7 |
| Cinnamon bark Oil | 0.7 |
| Orange Oil | 0.7 |
| Cedarwood Oil | 0.5 |
| Lemon Grass Oil | 0.5 |
| Surfactant | 2 |
| Water | Rest |

Formulation (E)

| Components | Percentage (%) |
| --- | --- |
| Geranium Oil | 3.7 |
| Lavender Oil | 1.4 |
| Neem | 1 |
| Eucalyptus Oil | 1 |
| Peppermint Oil | 1 |
| Cinnamon bark Oil | 0.9 |
| Orange Oil | 0.7 |
| Cedarwood Oil | 0.4 |
| Lemon Grass Oil | 0.4 |
| Surfactant | 2 |
| Water | Rest |

Formulation (F)

| Components | Percentage (%) |
| --- | --- |
| Geranium Oil | 2.1 |
| Peppermint Oil | 2.9 |
| Surfactant | 2 |
| Water | Rest |

The exemplary concentrated formulation is made by combining and thoroughly mixing the components. Ready-to-use formulation can be prepared by adding all ingredients, except water, to the surfactant while stirring thoroughly. Thereafter, desired percentage of final is prepared by adding the mixture to water while rapidly agitating.

Methods

The composition of the invention may be applied in areas that are infested with pests. Further, due to its lack of toxicity to humans and other animals, the composition may be applied in and around dwellings and other domestic areas. Areas include but are not limited to fields, homes, rooms, furniture, bedding, upholstery, vehicles, luggage, and fabrics including sheets.

The composition is effective against a wide range of chewing and sucking insects. The composition is particularly effective and useful to combat bed bugs of the species *Cimex lectularius*.

In one aspect, this invention relates to a substrate such as a fabric comprising the composition as described herein. In one embodiment, the fabric is a bedding. In one embodiment, the bedding is selected from the group consisting of a pillow, a sheet, a blanket, a mattress, a box spring, a pillowcase, a linen, a duvet, a comforter, a bedspread, a quilt, and a mattress cover. In one embodiment, the fabric is upholstery. In one embodiment, the upholstery is incorporated into a pillow or a piece of furniture. In one embodiment, the piece of furniture is a sofa, a chair, a settee, a bench, or a bed. In one embodiment, the fabric is a drapery, a tapestry, a rug, or a carpet. Other examples of substrates include flooring such as wood, laminates, tiles, stone, linoleum, and the like. Other substrates include walls, clothing, lights and lamps, etc. Targets for the materials and compositions include homes, hotels, motels, bedrooms, offices, medical offices, stores (e.g., furniture stores), animals (e.g., pets such as dogs and cats), gardens, agricultural planting areas, plants, etc.

EXAMPLES

The present invention is described with reference to the following examples, which are given by way of illustration and should not be construed to limit the scope of the present invention.

Example 1

A test was undertaken employing unconcealed bed bugs. One drop (about 25-30 mg) of test compound was applied to a filter paper and placed with a 16 oz. glass jar (3½ inches diameter×3% inches high) containing ten adult bed bugs (*Cimex lectularius*) of both sexes. The jar was then sealed with a plastic lid. Five replicates of ten bed bugs were exposed to each of the test compounds. The test formulations were assessed for 24 hour mortality. A control jar with no test compound was also included in the testing. The results were as follows.

TABLE 1

| Test Compound | 24 hr Mean Mortality % |
| --- | --- |
| Control | 0.0 |
| Formulation (A) | 77.2 |
| Formulation (B) | 77.1 |
| Formulation (C) | 85 |
| Formulation (D) | 89.6 |
| Formulation (E) | 91.8 |
| Formulation (F) | 83.8 |

Example 2

Figure 1D:
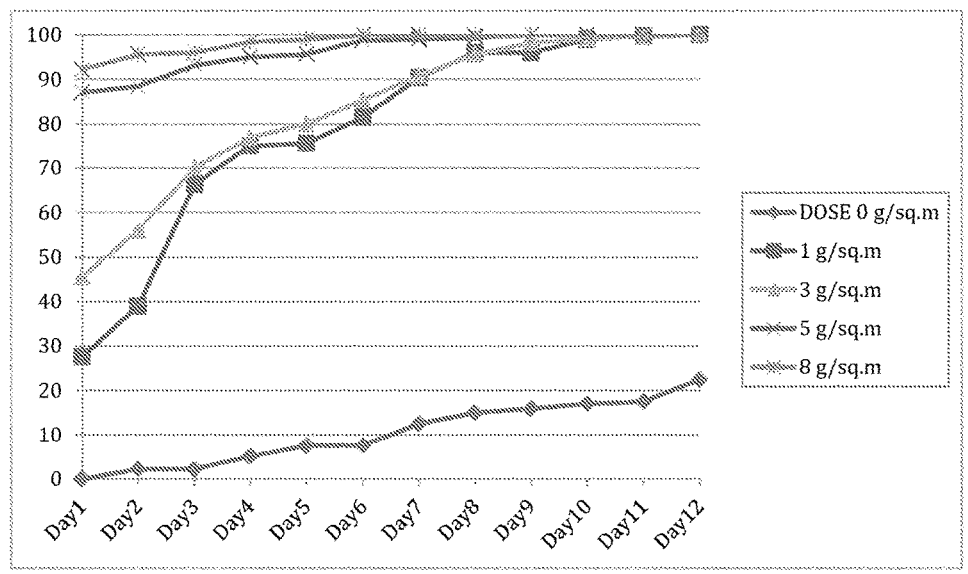

The bed bugs were exposed to FORMULATION-A on filter paper within Petri dishes. In each experiment, a variety of doses were used to establish optimal dose rates. Formulation A was applied at the dose rates equivalent to 1, 3, 5 and 8 g/sq·m. The surface area of the filter paper was calculated and the amount of FORMULATION-A required to treat the area at these rates determined. The measured quantity of FORMULATION-A was applied to the filter paper and spread evenly over the surface via a small paint brush. For each dose rate of formulation, ten bed bugs where exposed per Petri dish, with a total of four replicates (i.e. 40 bugs in total exposed per treatment). The controls consisted of four replicates of ten bugs on filter paper in Petri dishes not exposed to the FORMULATION-A (i.e. a further 40 bed bugs). Mortality was determined daily from 24 hours onwards by counting bed bugs that do not move after the dish is tapped. For each dose, the daily results were statistically compared with the control. The data for this experiment as it relates to Formulation A is shown in FIGS. 1A-1D.

Example 3

Figures 2A, 2B:
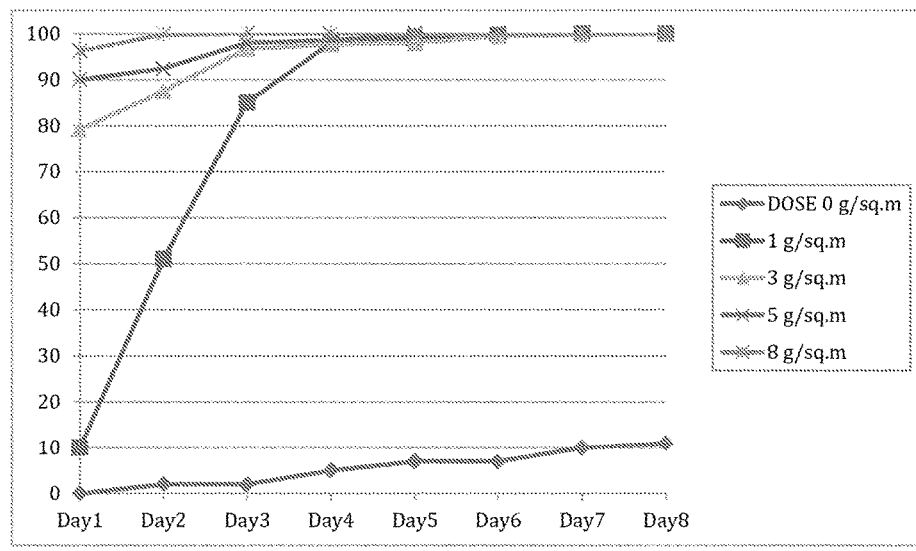
Figure 2D:
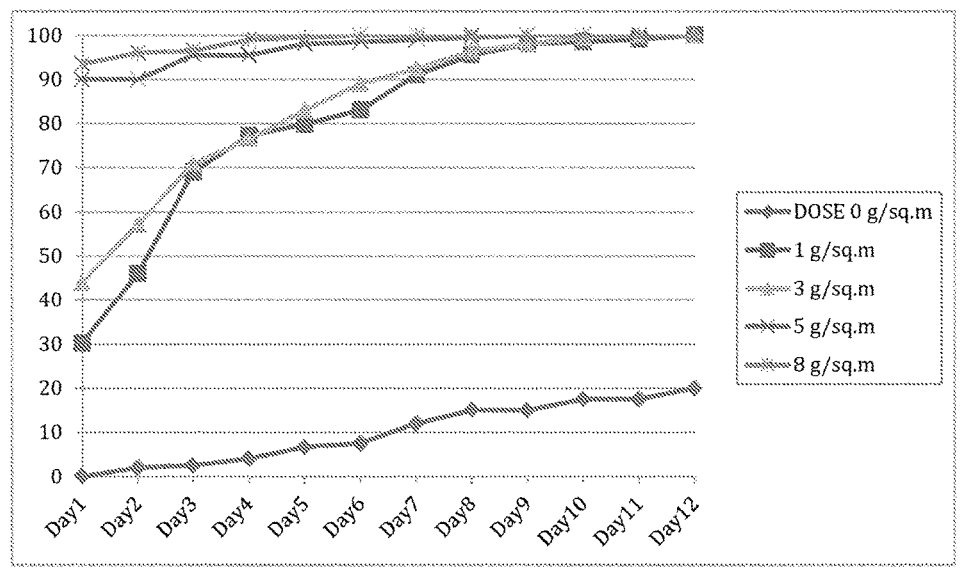

The bed bugs were exposed to residues of the FORMULATION-B on filter paper within Petri dishes. In each experiment, a variety of doses were used to establish optimal dose rates. Formulation B was applied at the dose rates equivalent to 1, 3, 5 and 8 g/sq·m. The surface area of the filter paper was calculated and the amount of formulation required to treat the area at these rates determined. The measured quantity of formulation was applied to the filter paper and spread evenly over the surface via a small paint brush. For each dose rate of FORMULATION-B, ten bed bugs where exposed per Petri dish, with a total of four replicates (i.e. 40 bugs in total exposed per treatment). The controls consisted of four replicates of ten bugs on filter paper in Petri dishes not exposed to the FORMULATION-B (i.e. a further 40 bed bugs). Mortality was determined daily from 24 hours onwards by counting bed bugs that do not move after the dish is tapped. For each dose, the daily results were statistically compared with the control. The data for this experiment as it relates to Formulation B is shown in FIGS. 2A-2D.

Example 4

Figures 3A, 3B:
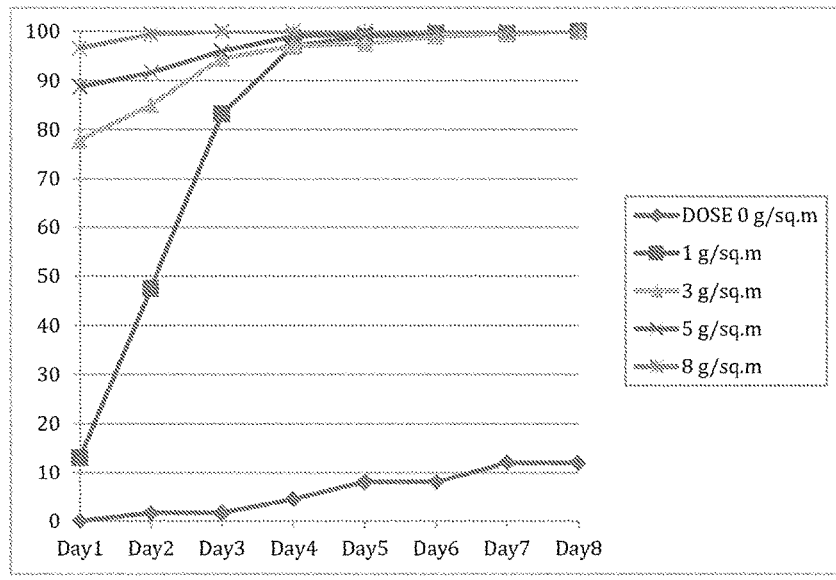
FIGS. 3A, 3B, 3C and 3D.
Figures 3C, 3D:
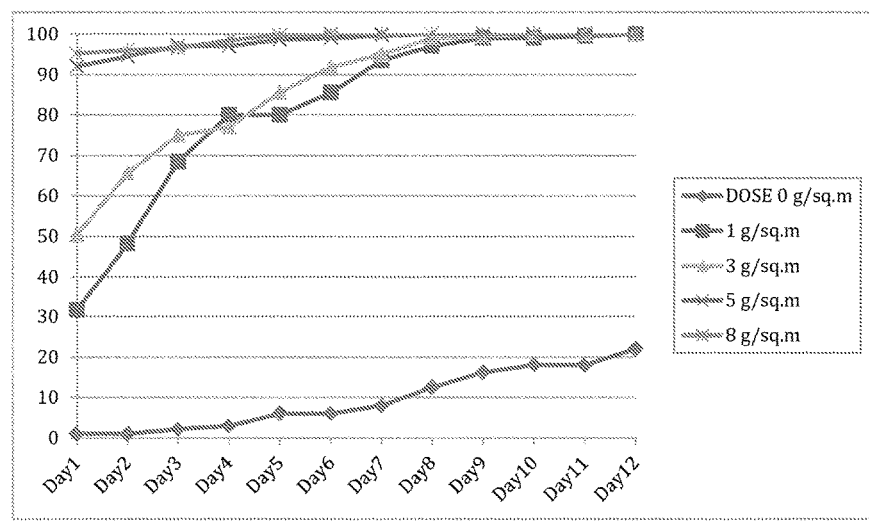

The bed bugs were exposed to residues of the FORMULATION-C on filter paper within Petri dishes. In each experiment, a variety of doses were used to establish optimal dose rates. The Formulation C were applied at the dose rates equivalent to 1, 3, 5 and 8 g/sq·m. The surface area of the filter paper was calculated and the amount of formulation required to treat the area at these rates determined. The measured quantity of formulation was applied to the filter paper and spread evenly over the surface via a small paint brush. For each dose rate of FORMULATION-C, ten bed bugs where exposed per Petri dish, with a total of four replicates (i.e. 40 bugs in total exposed per treatment). The controls consisted of four replicates of ten bugs on filter paper in Petri dishes not exposed to the FORMULATION-C (i.e. a further 40 bed bugs). Mortality was determined daily from 24 hours onwards by counting bed bugs that do not move after the dish is tapped. For each dose, the daily results were statistically compared with the control. The data for this experiment as it relates to Formulation C is shown in FIGS. 3A-3D.

Example 5

Figures 4A, 4B:
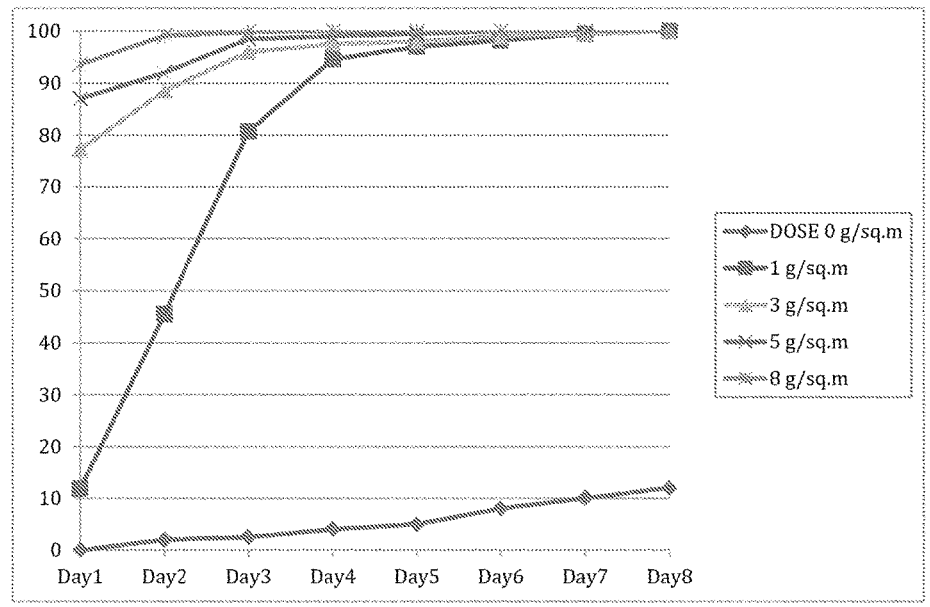
Figure 4D:
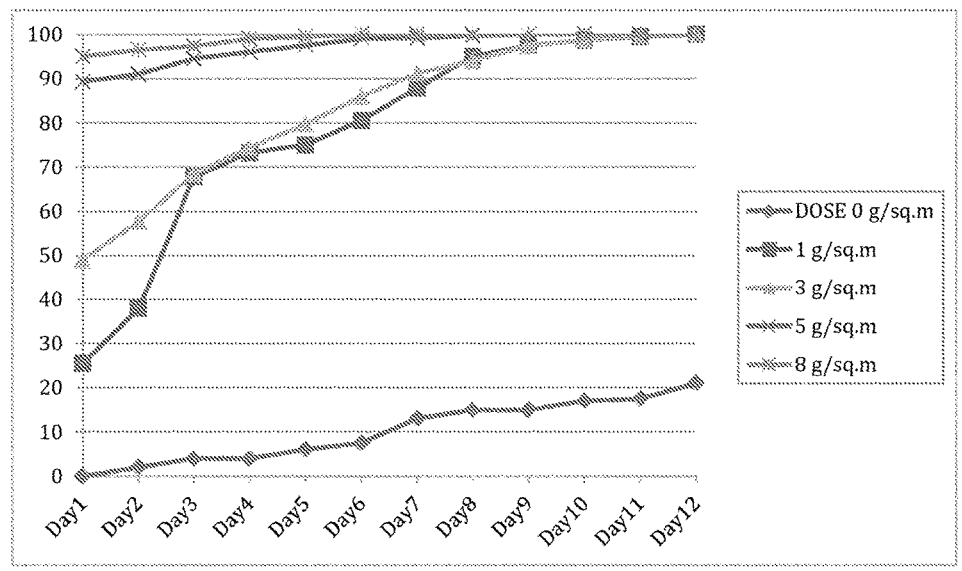

The bed bugs were exposed to residues of the FORMULATION-D on filter paper within Petri dishes. In each experiment, a variety of doses were used to establish optimal dose rates. The Formulation D were applied at the dose rates equivalent to 1, 3, 5 and 8 g/sq·m. The surface area of the filter paper was calculated and the amount of formulation required to treat the area at these rates determined. The measured quantity of formulation was applied to the filter paper and spread evenly over the surface via a small paint brush. For each dose rate of FORMULATION-D, ten bed bugs where exposed per Petri dish, with a total of four replicates (i.e. 40 bugs in total exposed per treatment). The controls consisted of four replicates of ten bugs on filter paper in Petri dishes not exposed to the FORMULATION—D (i.e. a further 40 bed bugs). Mortality was determined daily from 24 hours onwards by counting bed bugs that do not move after the dish is tapped. For each dose, the daily results were statistically compared with the control. The data for this experiment as it relates to Formulation D is shown in FIGS. 4A-4D.

Example 6

Figures 5A, 5B:
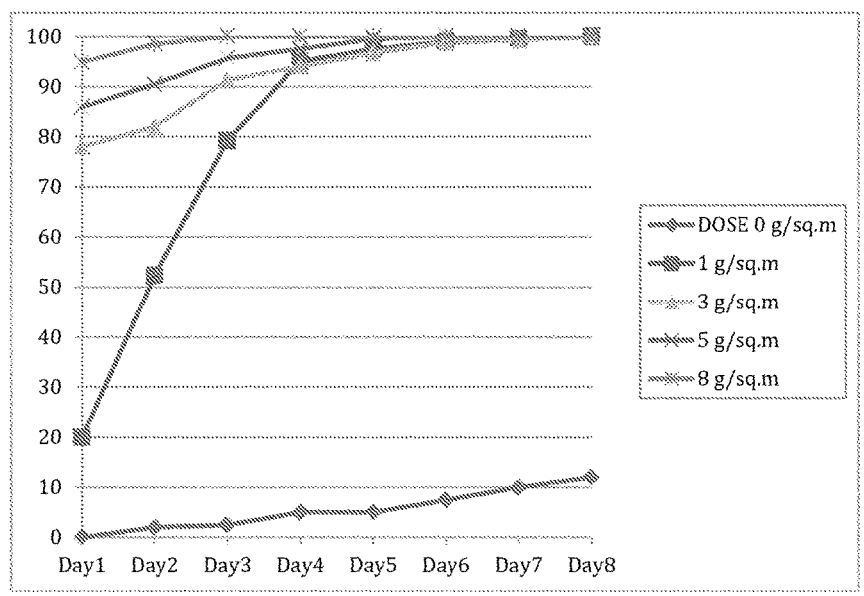
Figure 5D:
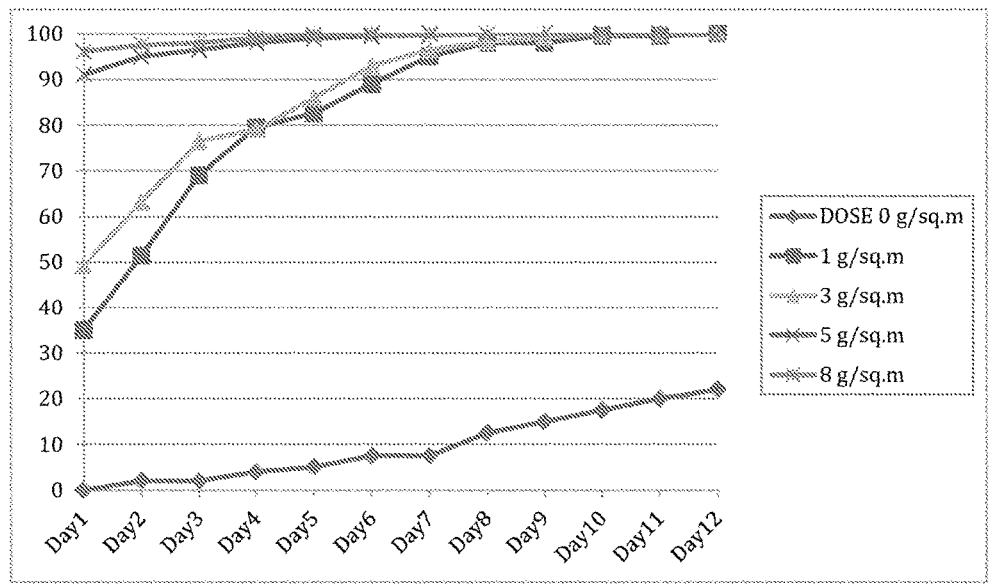

The bed bugs were exposed to the FORMULATION E on filter paper within Petri dishes. In each experiment, a variety of doses were used to establish optimal dose rates. The Formulation E were applied at the dose rates equivalent to 1, 3, 5 and 8 g/sq·m. The surface area of the filter paper was calculated and the amount of formulation required to treat the area at these rates determined. The measured quantity of formulation 6 was applied to the filter paper and spread evenly over the surface via a small paint brush. For each dose rate of FORMULATION-E, ten bed bugs where exposed per Petri dish, with a total of four replicates (i.e. 40 bugs in total exposed per treatment). The controls consisted of four replicates of ten bugs on filter paper in Petri dishes not exposed to the FORMULATION-E (i.e. a further 40 bed bugs). Mortality was determined daily from 24 hours onwards by counting bed bugs that do not move after the dish is tapped. For each dose, the daily results were statistically compared with the control. The data for this experiment as it relates to Formulation E is shown in FIGS. 5A-5D.

Example 7

Figures 6A, 6B:
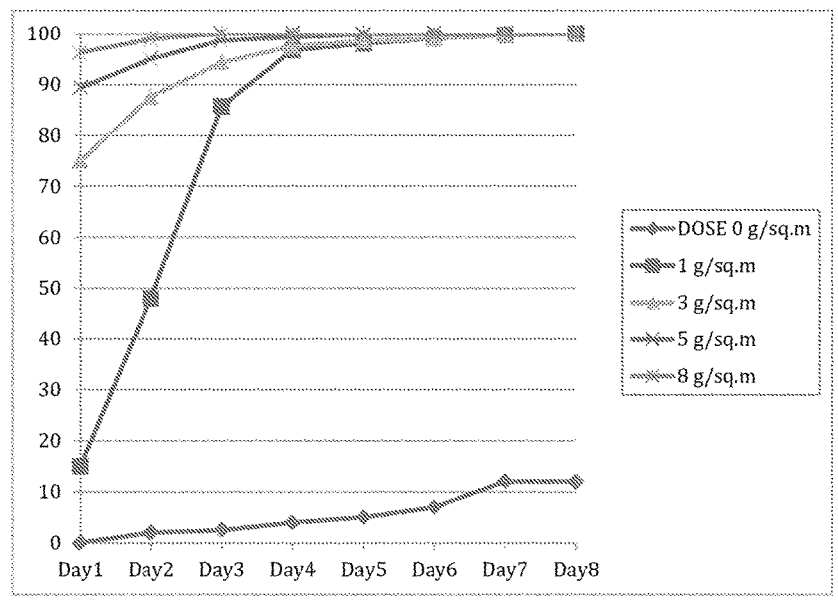
Figure 6D:
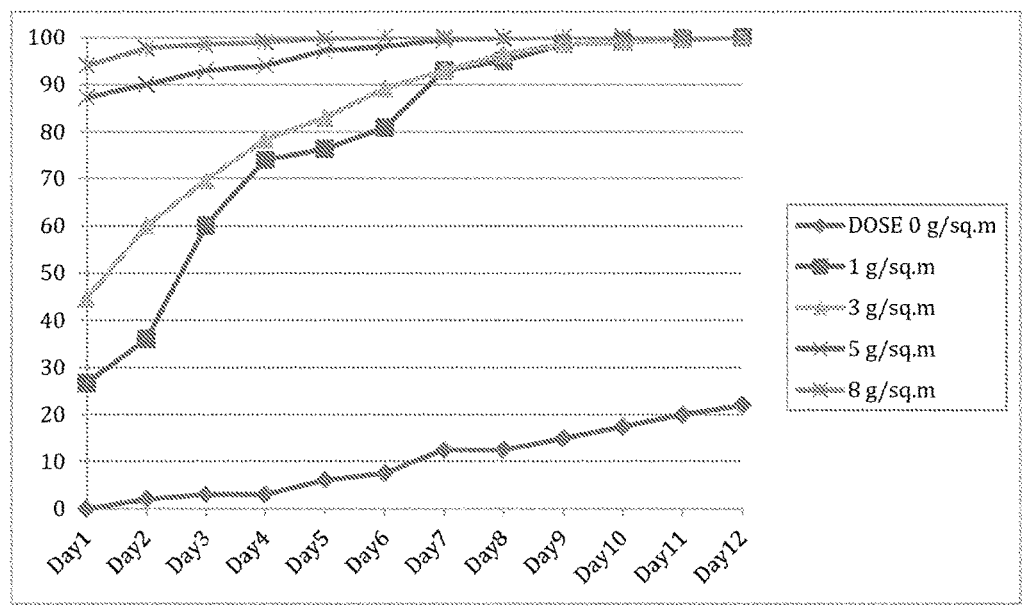

The bed bugs were exposed to the FORMULATION-F on filter paper within Petri dishes. In each experiment, a variety of doses were used to establish optimal dose rates. The Formulation F were applied at the dose rates equivalent to 1, 3, 5 and 8 g/sq·m. The surface area of the filter paper was calculated and the amount of formulation required to treat the area at these rates determined. The measured quantity of formulation-F was applied to the filter paper and spread evenly over the surface via a small paint brush. For each dose rate of FORMULATION, ten bed bugs where exposed per Petri dish, with a total of four replicates (i.e. 40 bugs in total exposed per treatment). The controls consisted of four replicates of ten bugs on filter paper in Petri dishes not exposed to the FORMULATION-F (i.e. a further 40 bed bugs). Mortality was determined daily from 24 hours onwards by counting bed bugs that do not move after the dish is tapped. For each dose, the daily results were statistically compared with the control. The data for this experiment as it relates to Formulation F is shown in FIGS. 6A-6D.

Example 8

Objective: To determine the overall killing efficacy of the bud bug test formulation against bed bugs (*Cimex lectularius*) and to determine the lowest percentage solution that will achieve 100% mortality within 30 minutes under the experimental conditions described herein.

Materials and Methods

Bed Bugs: The bed bugs (*Cimex lectularius*) used in this study were obtained from an established colony in the Entomology Department at the University of Kentucky, College of Agriculture. This colony originated from Fort Dix and has been maintained for 37 years without exposure to insecticides, and thus, possesses no resistance. Various bed bug stages were maintained at 25±5° C. in a dark chamber. Prior to testing, bed bugs were blood-fed every week to maintain health and collect eggs. Mortality tests were performed with 2-3$^{rd}$ instar bed bugs. Both sexes were used for these experiments and were also starved for at least two weeks prior to testing.

Procedure: A 7-cm filter paper was placed at the bottom of the cup to soak up excess spray residue and serve as the experimental arena. Tape was placed 1 cm from the edge of filter paper on all four edges to prevent bed bugs from leaving the testing arena (bed bugs will not crawl on celluloid tape), creating an effective treatment area of 5 cm×5 cm. A diagram of the experimental setup is shown in FIG. 7.

The filter paper with taped edges was placed at the bottom of a paper cup. Three bed bugs were introduced into the arena for testing for each replicate. The test solution and Envincio IC3 solutions were applied as a trigger spray from a 1-ft distance. The spray trigger was set to the "stream" setting. The Phantom® solution was applied as an aerosol from a 1 ft distance for 1 sec. Different concentrations of the test solution were applied to bed bugs to determine the lowest percentage solution that will kill 100% of the test individuals. Knockdown and mortality were recorded at various time intervals throughout a 30-minute period, and a minimum of four replicates were performed for each test solution.

Solutions: Various concentrations of the test solution were prepared in order to determine the lowest percentage solution that will kill 100% of the bed bugs in the arena. The industrial standards were applied at the highest concentrations suggested by their labels from the distances reported in the procedure. All solutions were diluted in deionized water.

Results

The kill efficacy results of the three concentrations of the test solution against bed bugs are presented in Table 2. These solutions were compared to two commercial standards, Envincio IC3® (applied as a trigger spray) and Phantom® (applied as an aerosol mist). The 10% test solution was the first solution to achieve 100% knockdown at 2 minutes. This was followed by the 8% solution and 5% solution, respectively. All test solutions achieved higher knockdown within less time than the commercial standards. In terms of mortality, the 10% solution was the most lethal to bed bugs and obtained 100% mortality at 1 minute. The 8% solution caused the second best mortality, achieving 58% mortality at 10 minutes. As with knockdown, all test solution concentrations caused higher mortality within 30 minutes than the commercial standards tested.

CONCLUSION

This report shows the efficacy of various concentration of test solution at killing bed bugs, compared to the two commercial standards. The results in this report show:

The 10% test solution kills 100% of the bed bugs within 1 minute in this experimental setup and out-performs all other solutions tested.

The lowest concentration of test solution that will kill 100% of the bed bugs in our experimental setup within 30 minutes is between 8% and 10%.

All test solution concentrations tested (5%, 8%, and 10%) outperformed the commercial standards within a 30-minute period in terms of overall knockdown and mortality.

TABLE 2

Bed Bug (*Cimex lectulcrius*) Knockdown and Mortality Results ± SEM
1 Ft. 1 Full Spray Test solution results: Test formulation & commercial standards

| | 0 Min | | 1 Min | | 2 Min | | 3 Min | |
|---|---|---|---|---|---|---|---|---|
| | KD | Mortality | KD | Mortality | KD | Mortality | KD | Mortality |
| 10% Solution | 83% ± 10% | 0% ± 0% | 100% ± 0% | 100% ± 0% | 100% ± 0% | 100% ± 0% | 100% ± 0% | 100% ± 0% |
| 8% Solution | 66% ± 14% | 0% ± 0% | 75% ± 9% | 33% ± 14% | 75% ± 9% | 33% ± 14% | 75% ± 9% | 41% ± 16% |
| 5% Solution | 58% ± 16% | 0% ± 0% | 58% ± 8% | 33% ± 14% | 50% ± 17% | 41% ± 8% | 66% ± 0% | 41% ± 8% |
| Phantom ® | 0% ± 0% | 0% ± 0% | 0% ± 0% | 0% ± 0% | 8% ± 4% | 0% ± 0% | 8% ± 4% | 0% ± 0% |
| Envincio IC3 ® | 0% ± 0% | 0% ± 0% | 58% ± 8% | 17% ± 5% | 58% ± 8% | 17% ± 5% | 58% ± 8% | 17% ± 5% |

| | 5 Min | | 10 Min | | 15 Min | | 30 Min | |
|---|---|---|---|---|---|---|---|---|
| | KD | Mortality | KD | Mortality | KD | Mortality | KD | Mortality |
| 10% Solution | 100% ± 0% | 100% ± 0% | 100% ± 0% | 100% ± 0% | 100% ± 0% | 100% ± 0% | 100% ± 0% | 100% ± 0% |
| 8% Solution | 75% ± 9% | 50% ± 17% | 75% ± 9% | 58% ± 8% | 75% ± 9% | 58% ± 8% | 66% ± 14% | 66% ± 14% |
| 5% Solution | 66% ± 0% | 50% ± 10% | 66% ± 0% | 50% ± 10% | 66% ± 0% | 50% ± 10% | 66% ± 0% | 50% ± 10% |
| Phantom ® | 25% ± 4% | 8% ± 4% | 33% ± 0% | 8% ± 4% | 33% ± 0% | 25% ± 4% | 33% ± 0% | 33% ± 0% |
| Envincio IC3 ® | 58% ± 8% | 50% ± 10% | 58% ± 8% | 17% ± 5% | 50% ± 11% | 17% ± 5% | 50% ± 11% | 17% ± 5% |

What is claimed is:

1. A method of controlling bed bugs, said method comprising applying a composition comprising a final concentration of about 2% to about 4% (v/v) geranium oil and at least one additional essential oil to a target area containing bed bugs.

2. The method of claim 1, wherein the at least one additional essential oil comprises peppermint oil, eucalyptus oil, clove oil, cinnamon oil, lavender oil, neem oil, orange oil, cedarwood oil, lemon grass oil, or a combination thereof.

3. The method of claim 1, wherein the final concentration of the at least one additional essential oil is between about 0.5% and about 4.9% (v/v).

4. The method of claim 1, further comprising a surface active agent.

5. The method of claim 4, wherein the surface active agent is castor oil or sodium lauryl sulfate.

6. The method of claim 5, wherein the surface active agent is castor oil, and further wherein the castor oil is ethoxylated.

7. The method of claim 1, wherein the composition is an oil-in-water emulsion or an aqueous formulation.

8. The method of claim 1, wherein the composition is a concentrated formulation, or a diluted formulation.

9. The method of claim 8, wherein the composition is a concentrated formulation.

10. The method of claim 9, wherein the final concentration is achieved by diluting the concentrated formulation between about 1:50 and about 1:500 with water prior to use.

11. The method of claim 1, wherein the composition comprises a final concentration of about 3% (v/v) geranium oil, about 0.8% (v/v) peppermint oil, about 0.4% (v/v) eucalyptus oil, about 0.9% (v/v) clove oil, about 0.8% (v/v) cinnamon bark oil, and about 2% (v/v) surfactant.

12. The method of claim 1, wherein the composition comprises a final concentration of about 2.9% (v/v) geranium oil, about 1% (v/v) neem oil, about 0.7% (v/v) orange oil, about 0.4% (v/v) eucalyptus oil, about 0.8% (v/v) clove oil, and about 4% (v/v) surfactant.

13. The method of claim 1, wherein the composition comprises a final concentration of about 4% (v/v) geranium oil, about 0.5% (v/v) neem oil, about 1.1% (v/v) peppermint oil, about 0.9% (v/v) eucalyptus oil, about 0.6% (v/v) lavender oil, about 0.4% (v/v) cedarwood oil, and about 1.5% (v/v) surfactant.

14. The method of claim 1, wherein the composition comprises a final concentration of about 2% (v/v) geranium oil, about 1.2% (v/v) lavender oil, about 1.2% (v/v) eucalyptus oil, about 0.7% (v/v) peppermint oil, about 0.7% (v/v) cinnamon bark oil, about 0.7% (v/v) orange oil, about 0.5% (v/v) cedarwood oil, about 0.5% (v/v) lemon grass oil, and about 2% (v/v) surfactant.

15. The method of claim 1, wherein the composition comprises a final concentration of about 3.7% (v/v) geranium oil, about 1.4% (v/v) lavender oil, about 1% (v/v) neem oil, about 1% (v/v) eucalyptus oil, about 1% (v/v) peppermint oil, about 0.9% (v/v) cinnamon bark oil, about 0.7% (v/v) orange oil, about 0.4% (v/v) cedarwood oil, about 0.4% (v/v) lemongrass oil, and about 2% (v/v) surfactant.

16. The method of claim 1, wherein the composition comprises a final concentration of about 2.1% (v/v) geranium oil, about 2.9% (v/v) peppermint oil, and about 2% (v/v) surfactant.

17. The method of claim 1, wherein the at least one additional essential oil comprises cedarwood oil.

18. The method of claim 17, wherein the composition comprises about 0.1% to about 10% (v/v) of cedarwood oil.

19. The method of claim 17, wherein the composition further comprises a surfactant.

* * * * *